(12) United States Patent
Wang et al.

(10) Patent No.: US 10,667,657 B2
(45) Date of Patent: Jun. 2, 2020

(54) STOOL DRAIN ASSEMBLY

(71) Applicant: Lien-Kung Wang, New Taipei (TW)

(72) Inventors: Han Ping Wang, New Taipei (TW);
Tai-Li Wang, New Taipei (TW);
Shun-Hsien Wang, New Taipei (TW)

(73) Assignee: Lien-Kung Wang, New Taipei (TW)

( * ) Notice: Subject to any disclaimer, the term of this patent is extended or adjusted under 35 U.S.C. 154(b) by 84 days.

(21) Appl. No.: 16/049,934

(22) Filed: Jul. 31, 2018

(65) Prior Publication Data
US 2020/0037832 A1    Feb. 6, 2020

(51) Int. Cl.
| A47K 17/00 | (2006.01) |
| G01N 1/04 | (2006.01) |
| G01N 1/34 | (2006.01) |
| A61B 10/00 | (2006.01) |
| A61F 5/442 | (2006.01) |
| A61F 5/451 | (2006.01) |
| A61F 5/44 | (2006.01) |

(52) U.S. Cl.
CPC .......... *A47K 17/00* (2013.01); *A61B 10/0038* (2013.01); *A61F 5/442* (2013.01); *A61F 5/4405* (2013.01); *A61F 5/451* (2013.01); *G01N 1/04* (2013.01); *G01N 1/34* (2013.01)

(58) Field of Classification Search
CPC ..... A61M 1/00; A61F 5/4405; A61B 10/0038
USPC ........................................................ 604/317
See application file for complete search history.

(56) References Cited

U.S. PATENT DOCUMENTS

| 5,730,147 A * | 3/1998 | Craig ................. | A61B 10/0038 |
| | | | 374/E13.002 |
| 8,016,816 B2 * | 9/2011 | Gregory .............. | A61M 3/0295 |
| | | | 604/540 |
| 2017/0020711 A1 * | 1/2017 | Nishtala ................ | A61M 39/10 |

* cited by examiner

*Primary Examiner* — Christine J Skubinna
(74) *Attorney, Agent, or Firm* — Cooper Legal Group, LLC

(57) ABSTRACT

A stool drain assembly including a main tube, an integrated connector, a potion or feces flushing water hole, a low-pressure balloon expansion water hole, at least two liquid pipes and a low-pressure balloon is provided. The main tube has a tube wall, an injection end and a water outlet. The integrated connector is disposed at the injection end and has a potion or feces flushing water injection cavity and an expansion water injection cavity. The potion or feces flushing water hole and the low-pressure balloon expansion water hole are arranged at the water outlet and are connected to the inside and outside of the tube wall respectively. At least two liquid pipes include a low-pressure balloon expansion liquid delivery pipe and a potion or feces flushing water liquid delivery pipe.

20 Claims, 11 Drawing Sheets

STOOL DRAIN ASSEMBLY

BACKGROUND OF THE INVENTION

Field of the Invention

The present invention relates to a stool drain assembly; and more particularly, the present invention relates to a stool drain assembly having a main tube of a special design, thereby providing a larger potion administration and treatment area for rectum and a large feces flushing area for rectum, and meanwhile integrating multiple cavities into a single connector.

Descriptions of the Related Art

A conventional way for dealing with fecal incontinence of patients openly needs to prevent risk of skin bedsore and cross infection of patients, and moreover, medical workers need to tolerate disgusting smell of the stool and maintain the dignity of the patients. Thus, this is not an easy issue to face with for both the patients and the medical workers.

On the other hand, although some manufactures have developed stool drain assemblies that can be placed within the anus to assist the medical workers or patients in discharging and dealing with the stool in a cleaner way, the stool drain assemblies have the following drawbacks in the manufacturing and actual operation thereof: when expansion water within a low-pressure balloon is extracted out, the low-pressure balloon will collapse and cover the water outlet so that the expansion water within the low-pressure balloon cannot be completely discharged and thus increases the difficulty in removing the low-pressure balloon from the anus; only a single potion or feces flushing water hole is provided, so large-area treatment and flushing cannot be achieved during the potion injection or flushing; a stool drain cavity, a potion injection cavity, a water injection cavity and a sampling cavity are independent components operating at dispersed positions, and each of the stool drain cavity, the potion injection cavity, the water injection cavity and the sampling cavity needs to be manufactured and assembled by multiple processes, so it is hard to reduce the production cost and the labor; and the stool drain cavity is directly connected with a stool collection bag, so the out-leakage of the stool is likely to occur during the replacement of the stool collection bag.

Accordingly, an urgent need exists in the art to provide a novel and improved stool drain assembly so as to effectively solve the aforesaid problems and save relevant processes and labor.

SUMMARY OF THE INVENTION

An objective of the present invention is to provide a stool drain assembly, an integrated connector of which integrates a potion or feces flushing water injection cavity, an expansion water injection cavity, a stool sampling port, a stool sampling port plug and a stool drain cavity into a single operational assembly, thereby effectively reducing the material cost and the labor. Moreover, the potion or feces flushing water injection cavity and the expansion water injection cavity are arranged at two opposite sides of the integrated connector respectively, and a thin tube for indicating excessive expansion is disposed at an injection valve of the expansion water injection cavity, so it can help to prevent medical workers from mistakenly injecting the potion or feces flushing water into the low-pressure balloon fixed at the vault of the rectum and thereby causing compressive damage of the rectum due to the rapid and excessive expansion of the low-pressure balloon.

Another objective of the present invention is to provide a stool drain assembly, a potion or feces flushing water hole of which comprises at least two auxiliary drain holes, and the arrangement of the at least two auxiliary drain holes can achieve the effect of injecting the potion into the whole rectal wall of a patient for large-area treatment, and meanwhile injecting the feces flushing water to a large area so as to soften the semi-solid stool and make it easy to be discharged.

Yet another objective of the present invention is to provide a stool drain assembly, an injection syringe of which that is used for preventing excessive expansion is provided with a water discharge hole at a scale marking of 46 ml for discharging excessive expansion water, thereby ensuring that the volume of the expansion water inside the injection syringe that is used for preventing excessive expansion is 45 ml. In this way, it can prevent more than 45 ml of water from being mistakenly injected into the low-pressure balloon, thereby preventing the compressive damage to the rectum caused by the rapid and excessive expansion of the low-pressure balloon.

A further objective of the present invention is to provide a stool drain assembly, a collection bag connector of which that can be opened or closed may be provided with a stool collection bag at a stool discharging port, and the collection bag connector that can be opened or closed controls the connection between a connection port thereof and the stool discharging port by the relative movement of a plunger within the collection bag connector that can be opened or closed, so the arrangement of the collection bag connector that can be opened or closed will have the effect of easy operation, preventing from being pulled out and being capable of completely enclosing the feces.

To achieve the aforesaid objectives, a stool drain assembly disclosed in the present invention comprises a main tube, an integrated connector, a potion or feces flushing water hole, a low-pressure balloon expansion water hole, at least two liquid pipes and a low-pressure balloon. The main tube has a tube wall extending along a length direction and an injection end and a water outlet disposed at two ends of the tube wall. The integrated connector is disposed at the injection end and has a potion or feces flushing water injection cavity and an expansion water injection cavity. The potion or feces flushing water hole is arranged at the water outlet and connected to the inside of the tube wall. The low-pressure balloon expansion water hole is arranged at the water outlet and connected to the outside of the tube wall. The at least two liquid pipes are disposed along the main tube and comprise a low-pressure balloon expansion liquid delivery tube and a potion or feces flushing water liquid delivery tube; the low-pressure balloon expansion liquid delivery tube is configured to connect the expansion water injection cavity and the low-pressure balloon expansion water hole, and the potion or feces flushing water liquid delivery tube is configured to connect the potion or feces flushing water injection cavity and the portion or feces flushing water hole. The low-pressure balloon is disposed at the water outlet of the main tube and has a chamber connected to the expansion water injection hole, and the expansion and contraction of the low-pressure balloon is adapted to be controlled by injecting expansion water into or extracting expansion water from the chamber, thereby placing the low-pressure balloon within the anus of the patient.

To achieve the aforesaid objective, the potion or feces flushing water hole included in the stool drain assembly of the present invention comprises at least two auxiliary drain holes, and the at least two drain holes are disposed between an external side of the tube wall and an internal diameter of a convex ring of the low-pressure balloon.

To achieve the aforesaid objective, one of the at least two auxiliary drain holes included in the stool drain assembly of the present invention shares the potion or feces flushing water liquid delivery pipe with the low-pressure balloon expansion water hole, and the one of the at least two auxiliary drain holes is not connected with the low-pressure balloon expansion water hole.

To achieve the aforesaid objective, the at least two auxiliary drain holes included in the stool drain assembly of the present invention are three auxiliary drain holes for discharging the injected potion or feces flushing water.

To achieve the aforesaid objective, the integrated connector having the multiple cavities included in the stool drain assembly of the present invention further comprises a stool sampling port, a stool sampling port plug and a stool drain cavity, the connection between the stool sampling port and the stool drain cavity can be controlled by the stool sampling port plug, and a syringe may be inserted into the stool sampling port to collect stool as a specimen under test, and the stool drain cavity is adapted to drain the stool from the main tube.

To achieve the aforesaid objective, the at least two liquid tubes included in the stool drain assembly of the present invention are embedded within the tube wall.

To achieve the aforesaid objective, a convex ring-shaped waterflow loop is arranged circularly within the chamber of the low-pressure balloon included in the stool drain assembly of the present invention.

To achieve the aforesaid objective, the stool drain assembly of the present invention further comprises a collection bag connector that can be opened or closed, wherein the collection bag connector that can be opened or closed has a connection port, a stool discharging port, and a plunger disposed between the connection port and the stool discharging port; the connection port is configured to connect the collection bag connector that can be opened or closed with the integrated connector, the stool discharging port is configured to be provided with a stool collection bag, and the plunger is configured to control the connection between the connection port and the stool discharging port so as to allow or limit the drainage of the feces liquid.

To achieve the aforesaid objective, the expansion water injection cavity of the integrated connector included in the stool drain assembly of the present invention injects expansion water by using an injection syringe for preventing excessive expansion, and the injection syringe for preventing excessive expansion has a water discharge hole at a scale marking of 46 ml.

To achieve the aforesaid objective, the expansion water injection cavity of the integrated connector having multiple cavities included in the stool drain assembly of the present invention is provided with a thin tube for indicating excessive expansion, and the thin tube for indicating excessive expansion is configured to cover an injection valve of the expansion water injection cavity so that medical workers can read the warnings of no more than 45 ml printed on the thin tube for indicating excessive expansion before injecting water with a syringe.

To achieve the aforesaid objective, the stool drain assembly of the present invention further comprises a temperature sensor, and the temperature sensor is embedded within the water outlet of the main tube.

The detailed technology and preferred embodiments implemented for the subject invention are described in the following paragraphs accompanying the appended drawings for people skilled in this field to well appreciate the features of the claimed invention.

DESCRIPTION OF THE PREFERRED EMBODIMENT

Figure 1:
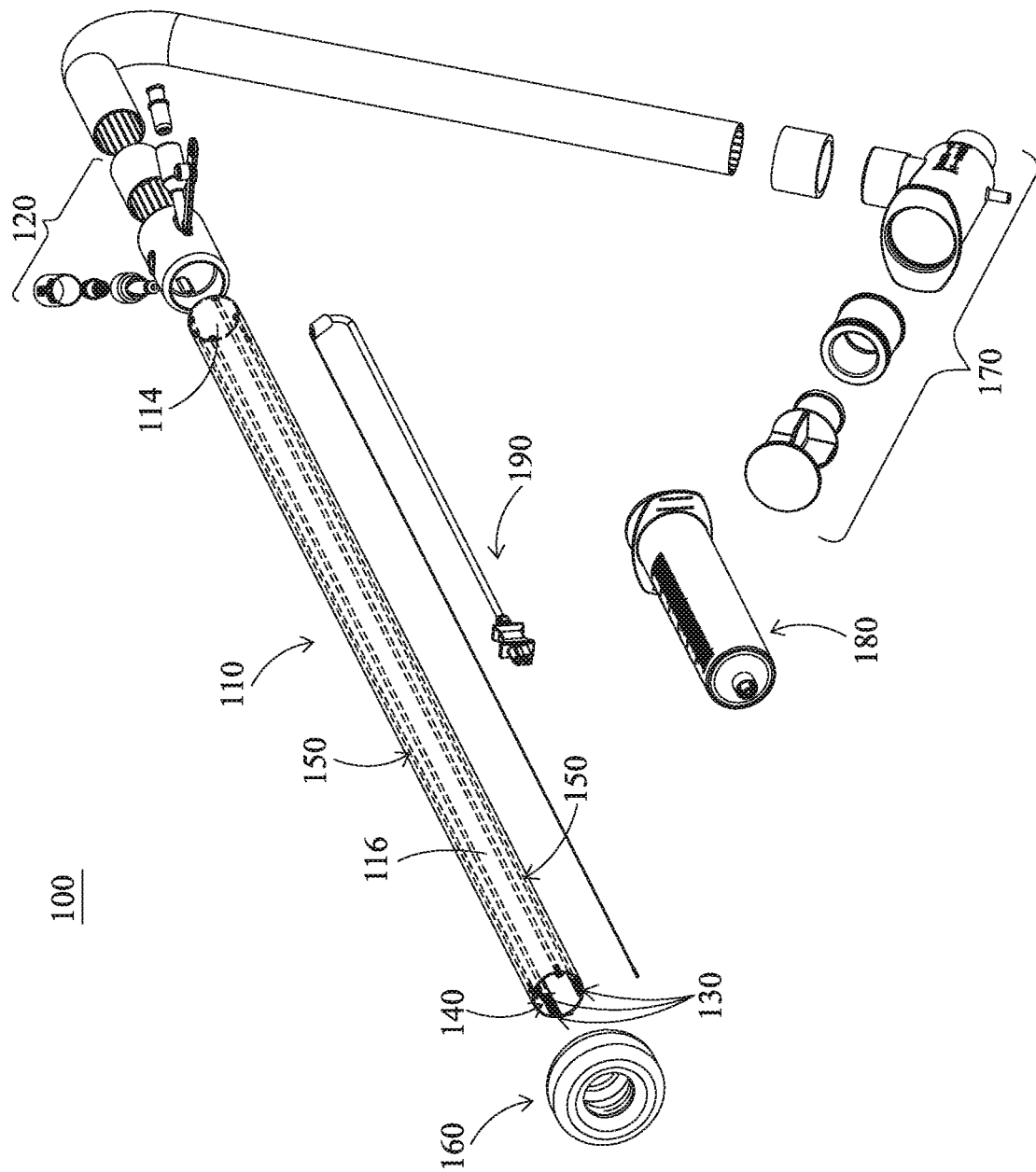
FIG. 1 is an exploded view of a stool drain assembly according to the present invention.
Figure 2:
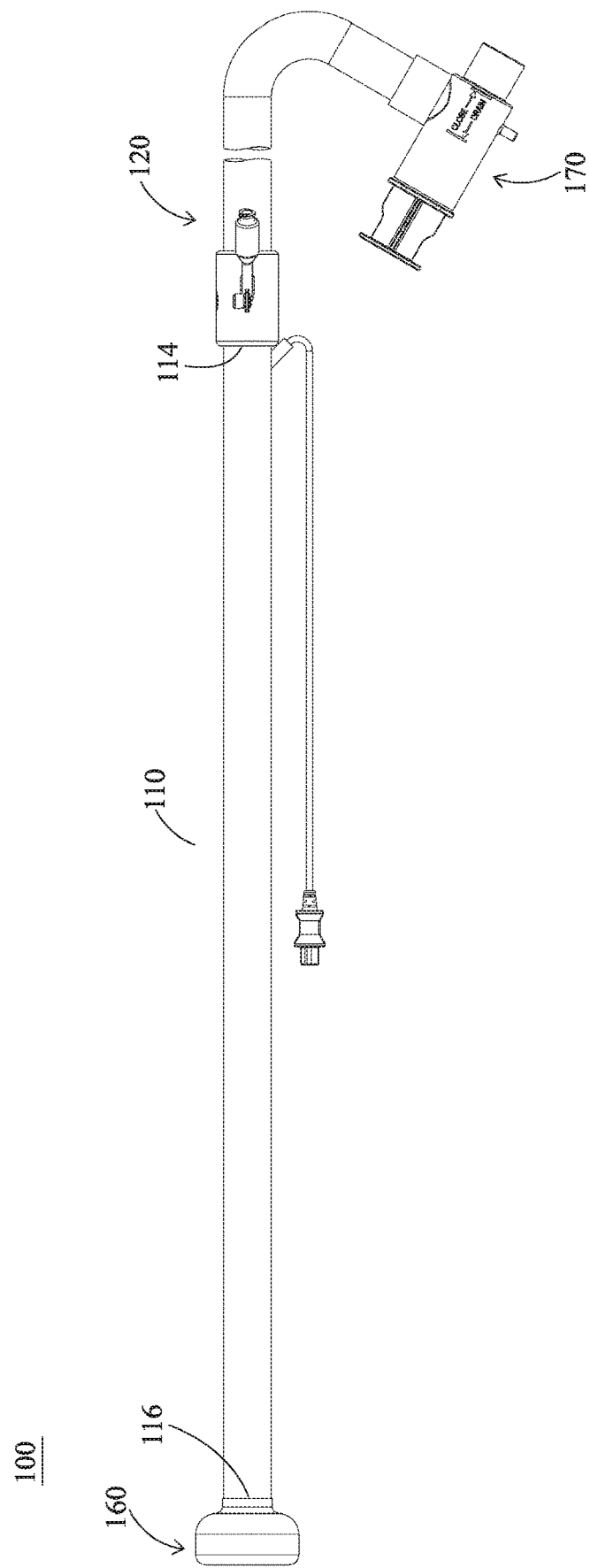
FIG. 2 is a schematic view illustrating the assembling of the stool drain assembly according to the present invention.

As shown in FIG. 1 and FIG. 2, a stool drain assembly 100 disclosed in the present invention is mainly constituted by a main tube 110, an integrated connector 120, a potion or feces flushing water hole 130, a low-pressure balloon expansion water hole 140, at least two liquid pipes 150 and a low-pressure balloon 160.

Figure 3:
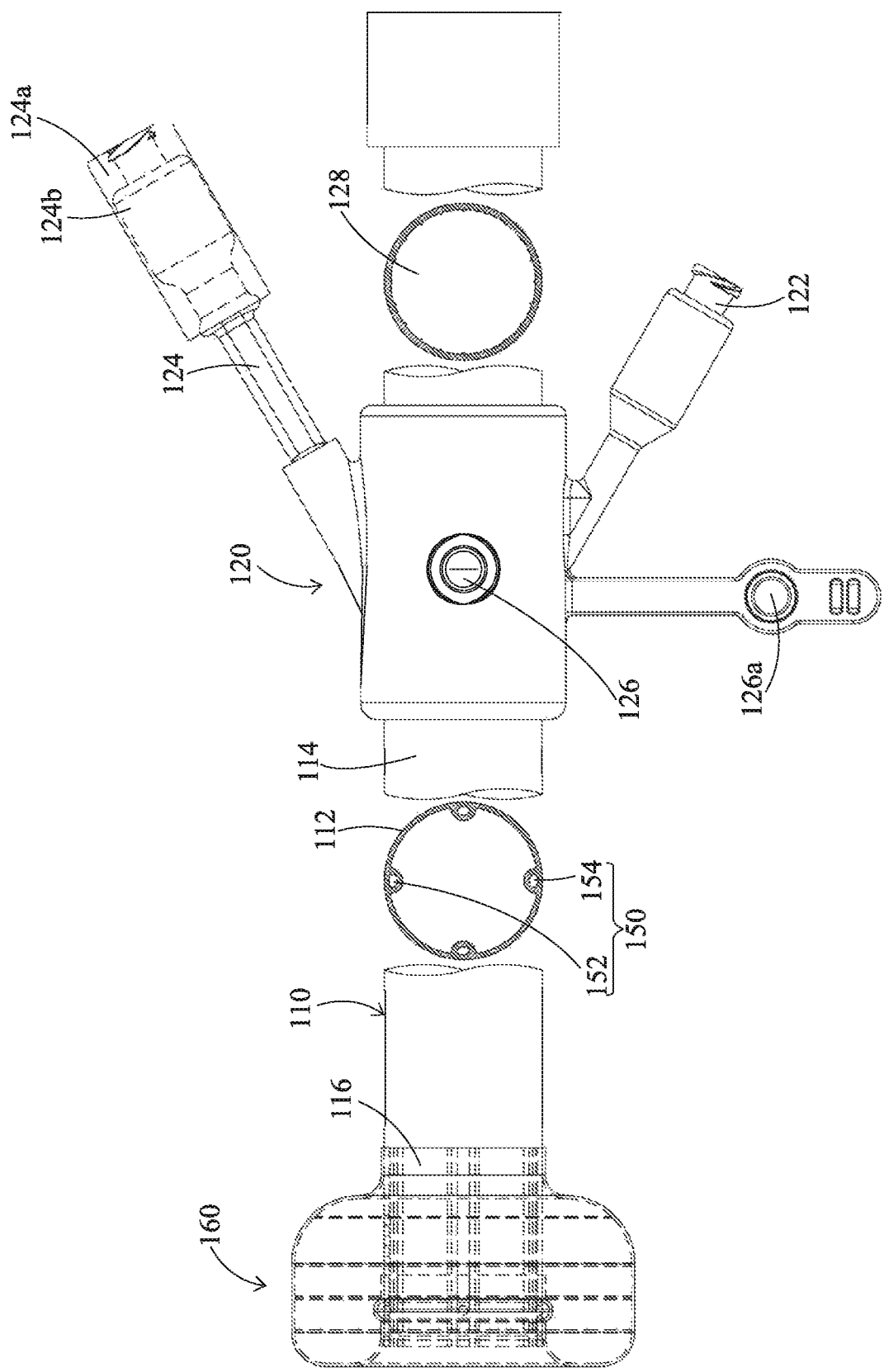
FIG. 3 is a side view of the stool drain assembly according to the present invention.
Figure 4:
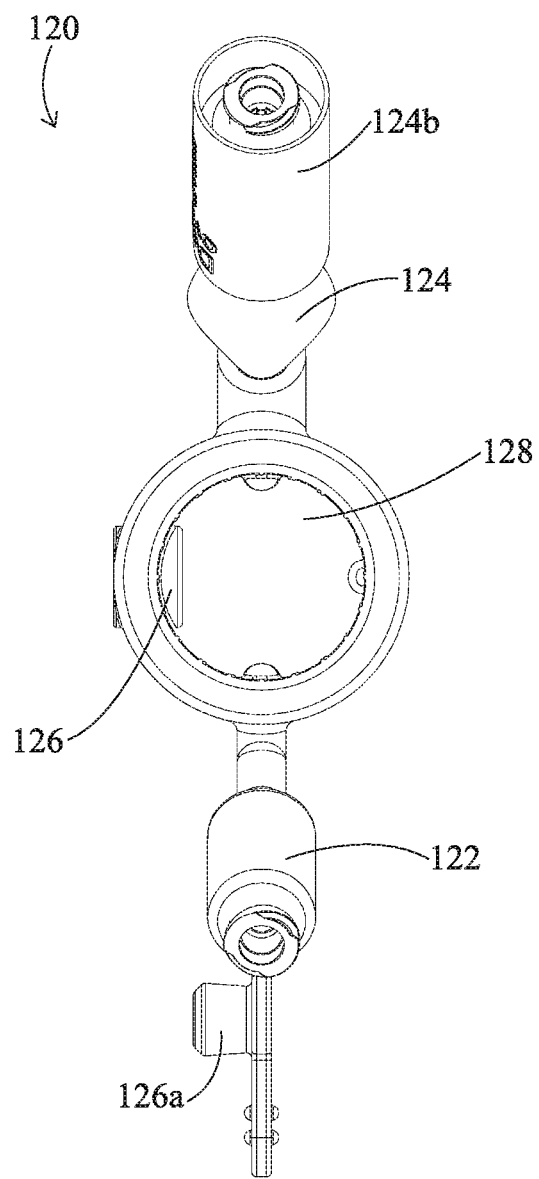
FIG. 4 is a back view of an integrated connector included in the stool drain assembly according to the present invention.
Figure 5:
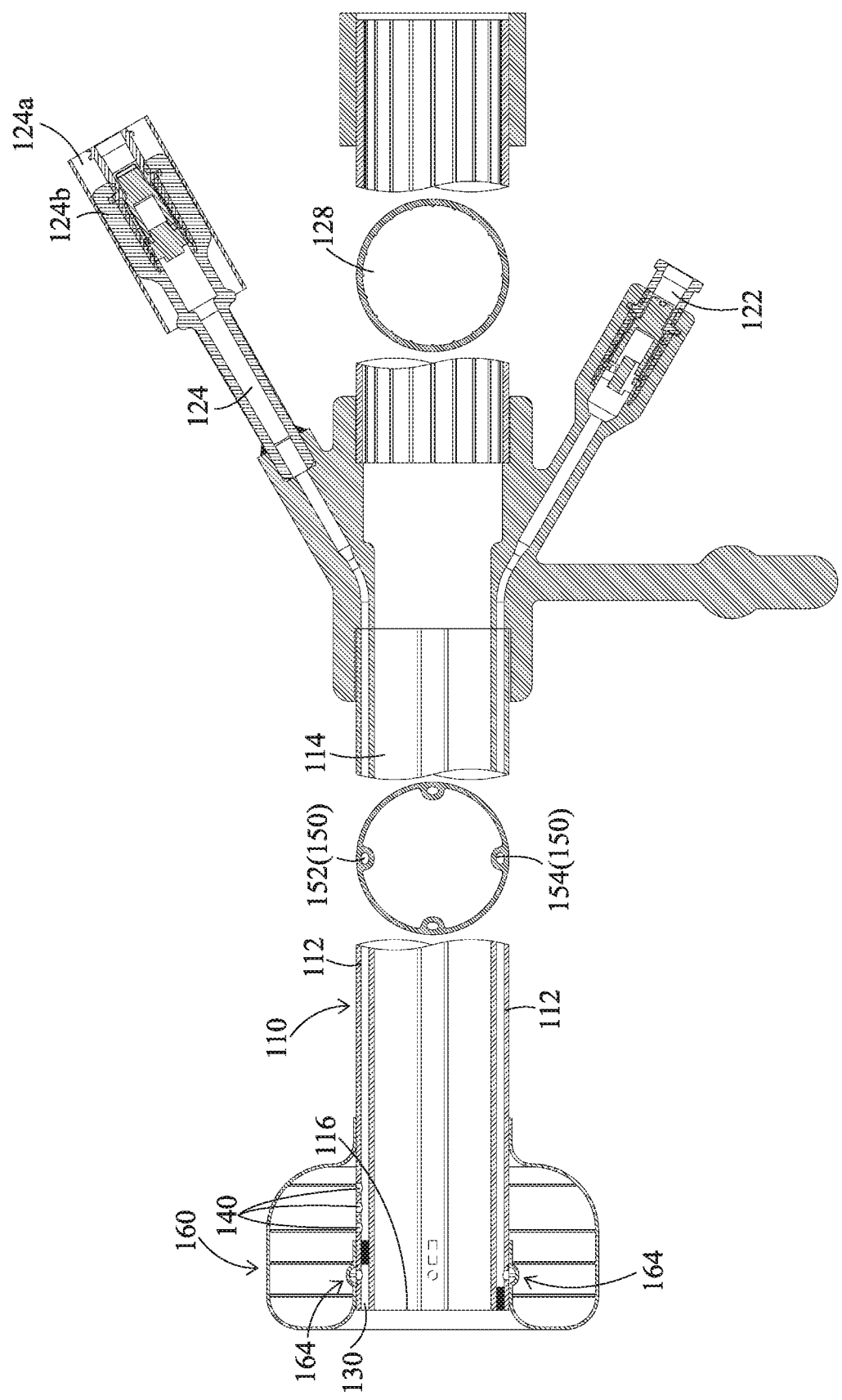
FIG. 5 is a side cross-sectional view of the stool drain assembly according to the present invention.
Figure 6:
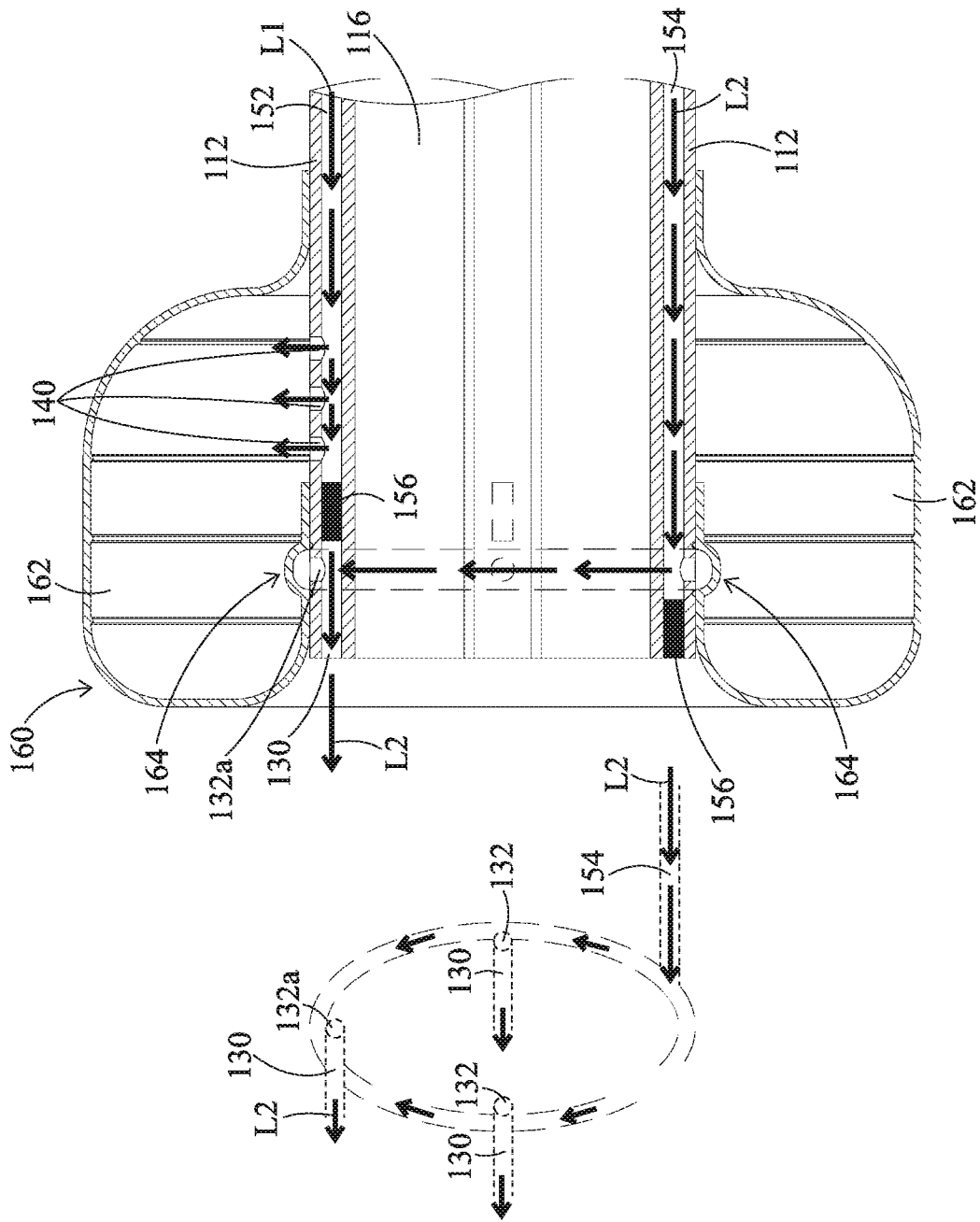
FIG. 6 is an enlarged schematic view of a low-pressure balloon shown in FIG. 5.

In detail, referring to FIG. 3 to FIG. 5 together, the main tube 110 has a tube wall 112 extending along a length direction and an injection end 114 (a right end) and a water outlet 116 (a left end) disposed at two ends of the tube wall 112. The integrated connector 120 is disposed at the side of the injection end 114 of the main tube 110 and has a potion or feces flushing water injection cavity 122 and an expansion water injection cavity 124. Additionally, as shown in FIG. 5 and FIG. 6, the potion or feces flushing water hole 130 is arranged at the water outlet 116 and connected to the inside of the tube wall 122, so the potion or feces flushing water hole 130 may be used to inject potion for treatment of anus of the patient or used to inject water or saline solution for feces flushing. The low-pressure balloon expansion water hole 140 is arranged at the water outlet 116 and connected to the outside of the tube wall 122.

Figure 7:
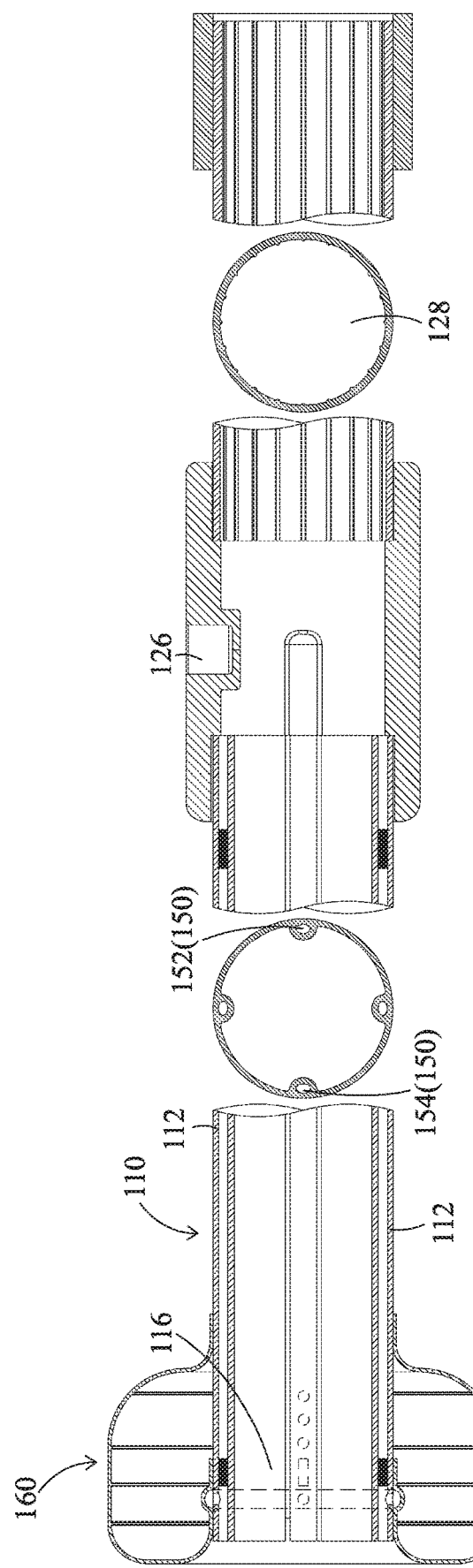
FIG. 7 is a top cross-sectional view of the stool drain assembly according to the present invention.

In the present invention, the at least two liquid pipes 150 are disposed along the main tube 110, and in an embodiment shown in FIG. 5 and FIG. 7, the at least two liquid pipes 150 comprise a low-pressure balloon expansion liquid delivery tube 152 and a potion or feces flushing water liquid delivery tube 154, the low-pressure balloon expansion liquid delivery tube 152 may be configured to connect the expansion water injection cavity 124 located above the right end (i.e., the injection end 114) of the main tube 110 and the low-pressure balloon expansion water hole 140 located above the left end (i.e., the water outlet 116) of the main tube 110, and the potion or feces flushing water liquid delivery tube 154 is configured to connect the potion or feces flushing water injection cavity 122 located below the right end (i.e., the injection end 114) of the main tube 110 and the portion or feces flushing water hole 130 located at the left end (i.e., the water outlet 116) of the main tube 110.

Figure 8:
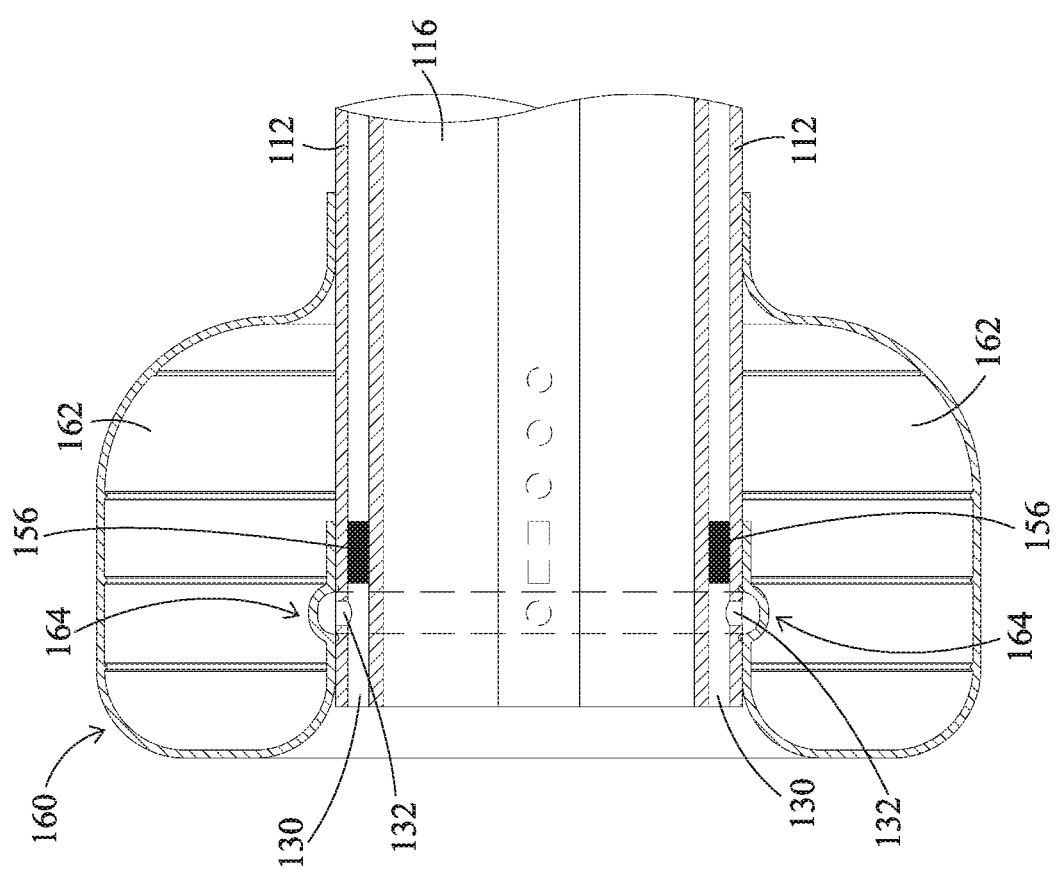
FIG. 8 is an enlarged schematic view of a low-pressure balloon shown in FIG. 7.
Figure 9:
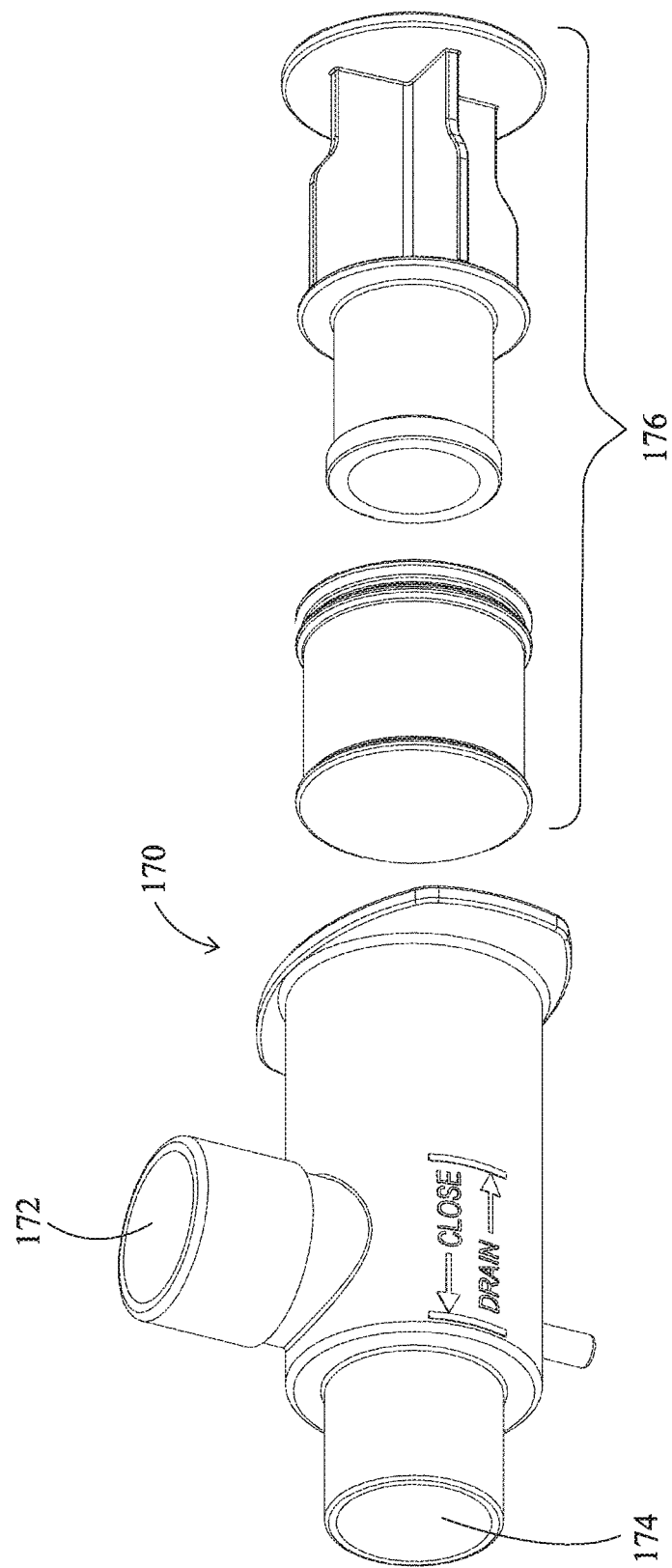
FIG. 9 is an exploded view of a collection bag connector that can be opened or closed included in the stool drain assembly according to the present invention.
Figure 10:
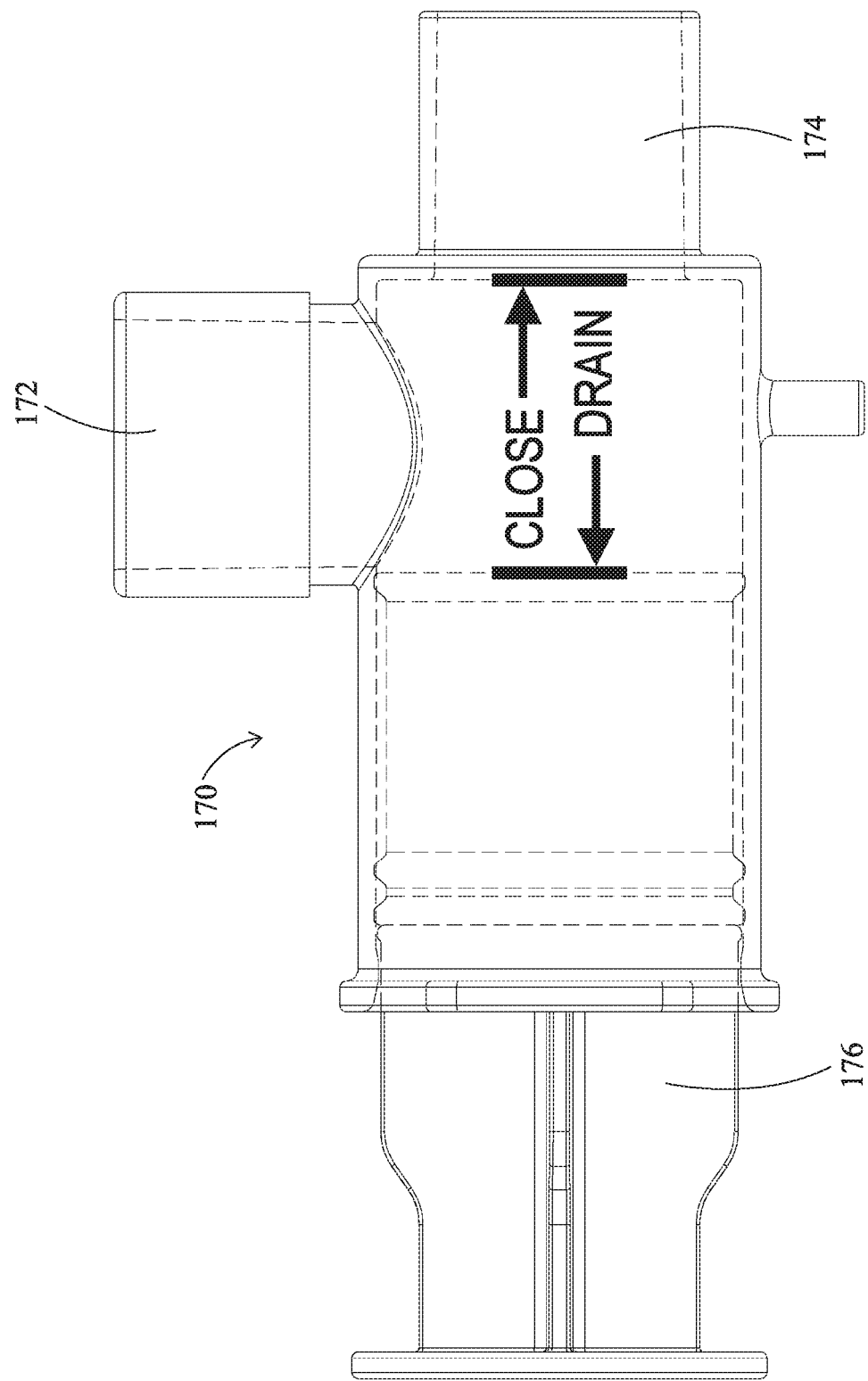
FIG. 10 is a side view of the collection bag connector that can be opened or closed included in the stool drain assembly according to the present invention.
Figure 11:
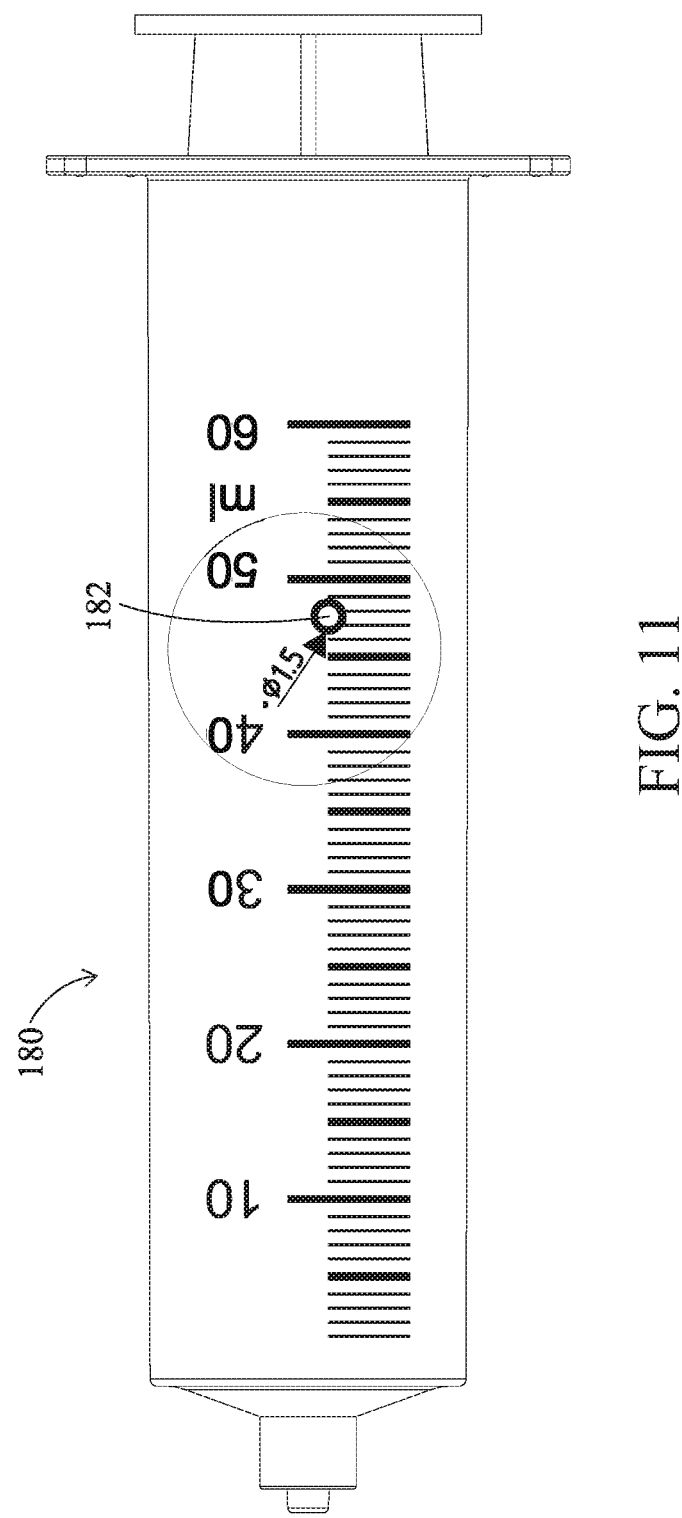
FIG. 11 is a schematic view of a drainage syringe included in the stool drain assembly according to the present invention.

As shown in FIG. 6 and FIG. 8, the low-pressure balloon 160 is disposed at the water outlet 116 of the main tube 110 and has a chamber 162 connected to the expansion water injection hole 140, and the expansion or contraction of the low-pressure balloon 160 is adapted to be controlled by injecting expansion water L1 into the chamber 162 or extracting the expansion water L1 from the chamber 162 so that it is convenient for a medical worker to place the low-pressure balloon 160 within the anus of the patient or remove the low-pressure balloon 160 from the anus of the patient. However, it shall be noted that, the volume of the expansion water L1 injected into the low-pressure balloon 160 needs to be limited to 45 ml or below 45 ml.

In the present invention, the potion or feces flushing water hole 130 located at the water outlet 116 of the main tube 110 comprises at least two auxiliary drain holes 132, and the at least two drain holes 132 are circularly disposed at the external side of the tube wall 112 in communication with each other (in more detail, disposed between the external side of the tube wall 122 and an internal diameter of a convex ring-shaped waterflow loop 164 of the low-pressure balloon 160). Therefore, in a preferred embodiment as shown in FIG. 6, the at least two auxiliary drain holes 132 are presented as three auxiliary drain holes 132 that are respectively located at an upper side, a left side and a right side of the water outlet 116, and the three auxiliary drain holes 132 are not only connected with each other but also connected with the potion or feces flushing water liquid delivery tube 154 (as shown in the left side of FIG. 6). In this way, when potion or feces flushing water L2 within the potion or feces flushing water injection cavity 122 is delivered from the right end (i.e., the injection end 114) of the main tube 110 to the left end (i.e., the water outlet 116) of the main tube 110 through the potion or feces flushing water liquid delivery tube 154, the potion or feces flushing water L2 is blocked by a blocking plug 156 after it reaches the lower side of the water outlet 116 and then proceeds towards the three auxiliary drain holes 132 that are connected with each other and thereby be discharged from the left side, the right side and the upper side of the water outlet 116.

Referring to FIG. 6 again, in the embodiment shown in FIG. 6, one of the three auxiliary drain holes 132 (i.e., an auxiliary drain hole 132a) shares the low-pressure balloon expansion liquid delivery pipe 152 with the low-pressure balloon expansion water hole 140, and another blocking plug 156 is installed within the low-pressure balloon expansion liquid delivery pipe 152 between the auxiliary drain hole 132a and the low-pressure balloon expansion water hole 140. In this way, although the auxiliary drain hole 132a shares the low-pressure balloon expansion liquid delivery pipe 152 with the low-pressure balloon expansion water hole 140, the auxiliary drain hole 132a is not connected with the low-pressure balloon expansion water hole 140.

In this way, by the arrangement of the three auxiliary drain holes 132, the medical worker can inject the potion into the whole rectal wall of the patient for large-area treatment, and meanwhile the medical worker can also inject the feces flushing water to a large area so as to soften the semi-solid stool and make it easy to be discharged, thereby improving the treatment scope and speed for the patient as compared to the prior art.

Referring to FIG. 3 and FIG. 4 together, in addition to the aforesaid potion or feces flushing water injection cavity 122 and the expansion water injection cavity 124, the integrated connector 120 further comprises a stool sampling port 126, a stool sampling port plug 126a and a stool drain cavity 128. The connection between the stool sampling port 126 and the stool drain cavity 128 may be controlled by the stool sampling port plug 126a, so the stool sampling port plug 126a is directly fastened onto the stool sampling port 126 when the sampling operation is not performed; and the stool drain cavity 128 is adapted to drain the stool from the main tube 110.

As shown in FIG. 5, since the potion or feces flushing water injection cavity 122 is disposed at the lower side of the integrated connector 120, the expansion water injection cavity 124 is disposed at the upper side of the integrated connector 120, and the potion or feces flushing water injection cavity 122, the expansion water injection cavity 124 and the stool drain cavity 128 are not connected with each other, the integrated connector 120 of the present invention can avoid mutual infection among the potion or feces flushing water injection cavity 122, the expansion water injection cavity 124 and the stool drain cavity 128 during the use thereof.

In a preferred embodiment of FIG. 5 and FIG. 7, because the low-pressure balloon expansion liquid delivery tube 152 and the potion or feces flushing water liquid delivery tube 154 comprised in the stool drain assembly 100 are directly embedded within the tube wall 112 of the main tube 110 during the injection moulding (i.e., the low-pressure balloon expansion liquid delivery tube 152 is embedded at the upper side within the tube wall 112 of the main tube 110, and the potion or feces flushing water liquid delivery tube 154 is embedded at the lower side within the tube wall 112 of the main tube 110), relevant manufacturing processes as well as labor cost can be reduced effectively. However, the low-pressure balloon expansion liquid delivery tube 152 and the potion or feces flushing water liquid delivery tube 154 may also be respectively disposed at external sides of the tube wall 112 of the main tube 110, and this can also achieve the same effect of connecting the right end (i.e., the injection end 114) of the main tube 110 with the left end (i.e., the water outlet 116) of the main tube 110.

The low-pressure balloon 160 included in the stool drain assembly 100 of this application is preferably made of a silicone material, but it is not limited thereto, and a convex ring-shaped waterflow loop 164 is arranged circularly within the chamber 162 of the low-pressure balloon 160. By the arrangement of the convex ring-shaped waterflow loop 164, when the expansion water L1 is extracted from the low-pressure balloon 160 in order to remove the low-pressure balloon 160 from the anus of the patient, the wall of the low-pressure balloon 160 that collapses inwardly due to the extraction of the expansion water L1 will be supported by the convex ring-shaped waterflow loop 164, thereby preventing the wall collapsed from covering or blocking the low-pressure balloon expansion water hole 140 and thus making it difficult or impossible to remove the expansion water L1 from the cavity 162. In this way, the removal of the low-pressure balloon 160 from the patient can be facilitated.

The stool drain assembly 100 further comprises a collection bag connector 170 that can be opened or closed. The collection bag connector 170 that can be opened or closed has a connection port 172, a stool discharging port 174, and a plunger 176 disposed between the connection port 172 and the stool discharging port 174. The connection port 172 is configured to be connected with the integrated connector 120, the stool discharging port 174 is configured to be provided with a stool collection bag (not shown), and the plunger 176 is configured to control the connection between the connection port 172 and the stool discharging port 174. By the pushing in and pulling out of the plunger 176 comprised in the collection bag connector 170 that can be opened or closed, the stool drain assembly 100 of the present invention will have the effect of easy operation, preventing from being pulled out and being capable of completely enclosing the feces.

The expansion water L1 is injected with an injection syringe by the medical worker in the prior art, so the injection syringe is improved by the present invention to ensure that the volume of the injected expansion water L1 will not exceed the prescribed standard volume. In detail, when the expansion water L1 in the expansion water injection cavity 124 of the integrated connector 120 of the present invention is injected into the low-pressure balloon 160 by an injection syringe 180 for preventing excessive expansion, the injection syringe 180 for preventing excessive expansion is provided with a water discharge hole 182 at a scale marking slightly above 46 ml for discharging excessive expansion water L1, thereby ensuring that the volume of the expansion water inside the injection syringe for preventing excessive expansion is 45 ml. In this way, it can prevent more than 45 ml of water from being mistakenly injected into the low-pressure balloon 160, thereby preventing the compressive damage to the rectum caused by the rapid and excessive expansion of the low-pressure balloon 160.

For preventing the excessive expansion of the low-pressure balloon 160, the present invention further comprises another protection measurement. That is, a thin tube 124a for indicating excessive expansion is additionally disposed at the expansion water injection cavity 124 of the integrated connector 120. The thin tube 124a for indicating excessive expansion is a secondary insurance for preventing excessive water from being injected into the low-pressure balloon 160. In detail, the thin tube 124a for indicating excessive expansion may be printed with words of "Do not overfill ≤45 ml" and cover a valve head of the expansion water injection cavity 124 so as to force the medical worker to read the warnings of excessive expansion printed on the surface of the thin tube before water or potion injection, thereby achieving the effect of warning.

The stool drain assembly 100 may further selectively comprise a temperature sensor 190, and the temperature sensor 190 is embedded within the water outlet 116 of the main tube 110 so that the temperature at the anus of the patient can be monitored at any time to perform corresponding medical operations.

According to the above description, because the integrated connector 120 included in the stool drain assembly 100 of the present invention integrates the potion or feces flushing water injection cavity 122, the expansion water injection cavity 124, the stool sampling port 126, the stool sampling port plug 126a and the stool drain cavity 128 into a single operational assembly, the material cost and the labor required can be effectively reduced during the production process. Moreover, in the preferred embodiments shown in the figures, the potion or feces flushing water injection cavity 122 and the expansion water injection cavity 124 are arranged at two opposite sides of the integrated connector 120 respectively, and the thin tube 124a for indicating excessive expansion is disposed at the expansion water injection cavity 124, so the aforesaid design details can also help to prevent medical workers from mistakenly injecting the potion or feces flushing water L2 into the low-pressure balloon 160 fixed at the vault of the rectum and thereby causing compressive damage of the rectum due to the rapid and excessive expansion of the low-pressure balloon 160. Moreover, the injection syringe 180 for preventing excessive expansion may also be provided with the water discharge hole 182 at a scale marking of 46 ml for discharging the excessive expansion water L1, thereby ensuring that the volume of the expansion water inside the injection syringe 180 for preventing excessive expansion is 45 ml to maintain the pressure within the low-pressure balloon 160.

On the other hand, by the arrangement of the three auxiliary drain holes 132, the medical worker can inject the potion into the whole rectal wall of the patient for large-area treatment simply by a single operation, and meanwhile the medical worker can also inject the feces flushing water to a large area simply by a single operation so as to soften the semi-solid stool and make it easy to be discharged, thereby significantly improving the treatment scope and speed for the patient as compared to the stool drain assembly currently available.

Finally, The collection bag connector 170 that can be opened or closed may control the connection between the collection bag connector 170 that can be opened or closed and the stool collection bag 178 by the plunger 176. Thus, by the arrangement of the plunger 176, the collection bag connector 170 that can be opened or closed will have the effect of easy operation, preventing from being pulled out and being capable of completely enclosing the feces, thereby increasing the convenience in replacing the stool collection bag 178.

The above disclosure is related to the detailed technical contents and inventive features thereof. People skilled in this field may proceed with a variety of modifications and replacements based on the disclosures and suggestions of the invention as described without departing from the characteristics thereof. Nevertheless, although such modifications and replacements are not fully disclosed in the above descriptions, they have substantially been covered in the following claims as appended.

What is claimed is:

1. A stool drain assembly being configured to drain and collect stool of a patient, comprising:
   a main tube, having a tube wall extending along a length direction and an injection end and a water outlet disposed at two ends of the tube wall;
   an integrated connector, being disposed at the injection end and having multiple cavities including a potion or feces flushing water injection cavity and an expansion water injection cavity;
   a potion or feces flushing water hole, being arranged at the water outlet and connected to an inside of the tube wall;
   a low-pressure balloon expansion water hole, being arranged at the water outlet and connected to an outside of the tube wall;
   at least two liquid pipes, being disposed along the main tube and comprising a low-pressure balloon expansion liquid delivery tube and a potion or feces flushing water liquid delivery tube, the low-pressure balloon expansion liquid delivery tube being configured to connect the expansion water injection cavity and the low-pressure balloon expansion water hole, the potion or feces flushing water liquid delivery tube being configured to connect the potion or feces flushing water injection cavity and the potion or feces flushing water hole; and a low-pressure balloon, being disposed at the water outlet of the main tube and having a chamber connected to the expansion water injection cavity, expansion and contraction of the low-pressure balloon being adapted to be controlled by injecting expansion water into or extracting expansion water from the chamber;

wherein the potion or feces flushing water hole comprises at least two auxiliary drain holes, and the at least two auxiliary drain holes are disposed between the outside of the tube wall and an internal diameter of a convex ring-shaped waterflow loop of the low-pressure balloon.

2. The stool drain assembly of claim 1, wherein one of the at least two auxiliary drain holes shares the low-pressure balloon expansion liquid delivery tube with the low-pressure balloon expansion water hole, and the one of the at least two auxiliary drain holes is not connected with the low-pressure balloon expansion water hole.

3. The stool drain assembly of claim 2, wherein the at least two auxiliary drain holes are three auxiliary drain holes for discharging the potion or feces flushing water.

4. The stool drain assembly of claim 1, wherein the integrated connector having the multiple cavities further comprises a stool sampling port, a stool sampling port plug and a stool drain cavity, a connection between the stool sampling port and the stool drain cavity configured to be controlled by the stool sampling port plug, and the stool sampling port configured to receive a syringe to collect stool from the main tube as a specimen under test.

5. The stool drain assembly of claim 1, wherein the at least two liquid pipes are embedded within the tube wall.

6. The stool drain assembly of claim 1, wherein the convex ring-shaped waterflow loop is arranged circularly within the chamber of the low-pressure balloon.

7. The stool drain assembly of claim 1, further comprising a collection bag connector configured to be opened or closed, wherein the collection bag connector configured to be opened or closed has a connection port, a stool discharging port, and a plunger disposed between the connection port and the stool discharging port, the connection port is configured to be connected with the integrated connector, the stool discharging port is configured to be provided with a stool collection bag, and the plunger is configured to control a connection between the connection port and the stool discharging port.

8. The stool drain assembly of claim 1, wherein the expansion water injection cavity of the integrated connector injects expansion water by using an injection syringe for preventing excessive expansion, and the injection syringe for preventing excessive expansion has a water discharge hole at a scale marking above 46 ml.

9. The stool drain assembly of claim 1, wherein the expansion water injection cavity of the integrated connector is provided with a thin tube for indicating excessive expansion, and the thin tube for indicating excessive expansion covers an injection valve of the expansion water injection cavity so as to force medical workers to read the warnings of excessive expansion printed on the thin tube before injecting water with a syringe.

10. The stool drain assembly of claim 1, further comprising a temperature sensor, wherein the temperature sensor is embedded within the water outlet of the main tube.

11. A stool drain assembly being configured to drain and collect stool of a patient, comprising:

a main tube, having a tube wall extending along a length direction and an injection end and a water outlet disposed at two ends of the tube wall;

an integrated connector, being disposed at the injection end and having multiple cavities including a potion or feces flushing water injection cavity and an expansion water injection cavity;

a potion or feces flushing water hole, being arranged at the water outlet and connected to an inside of the tube wall;

a low-pressure balloon expansion water hole, being arranged at the water outlet and connected to an outside of the tube wall;

at least two liquid pipes, being disposed along the main tube and comprising a low-pressure balloon expansion liquid delivery tube and a potion or feces flushing water liquid delivery tube, the low-pressure balloon expansion liquid delivery tube being configured to connect the expansion water injection cavity and the low-pressure balloon expansion water hole, the potion or feces flushing water liquid delivery tube being configured to connect the potion or feces flushing water injection cavity and the potion or feces flushing water hole; and a low-pressure balloon, being disposed at the water outlet of the main tube and having a chamber connected to the expansion water injection cavity, expansion and contraction of the low-pressure balloon being adapted to be controlled by injecting expansion water into or extracting expansion water from the chamber;

wherein the integrated connector having the multiple cavities further comprises a stool sampling port, a stool sampling port plug and a stool drain cavity, a connection between the stool sampling port and the stool drain cavity configured to be controlled by the stool sampling port plug, and the stool sampling port configured to receive a syringe to collect stool from the main tube as a specimen under test.

12. The stool drain assembly of claim 11, wherein a convex ring-shaped waterflow loop is arranged circularly within the chamber of the low-pressure balloon.

13. The stool drain assembly of claim 11, further comprising a collection bag connector configured to be opened or closed, wherein the collection bag connector configured to be opened or closed has a connection port, a stool discharging port, and a plunger disposed between the connection port and the stool discharging port, the connection port is configured to be connected with the integrated connector, the stool discharging port is configured to be provided with a stool collection bag, and the plunger is configured to control a connection between the connection port and the stool discharging port.

14. The stool drain assembly of claim 11, wherein the expansion water injection cavity of the integrated connector injects expansion water by using an injection syringe for preventing excessive expansion, and the injection syringe for preventing excessive expansion has a water discharge hole at a scale marking above 46 ml.

15. The stool drain assembly of claim 11, further comprising a temperature sensor, wherein the temperature sensor is embedded within the water outlet of the main tube.

16. A stool drain assembly being configured to drain and collect stool of a patient, comprising:

a main tube, having a tube wall extending along a length direction and an injection end and a water outlet disposed at two ends of the tube wall;

an integrated connector, being disposed at the injection end and having multiple cavities including a potion or feces flushing water injection cavity and an expansion water injection cavity;

a potion or feces flushing water hole, being arranged at the water outlet and connected to an inside of the tube wall;

a low-pressure balloon expansion water hole, being arranged at the water outlet and connected to an outside of the tube wall;

at least two liquid pipes, being disposed along the main tube and comprising a low-pressure balloon expansion liquid delivery tube and a potion or feces flushing water liquid delivery tube, the low-pressure balloon expansion liquid delivery tube being configured to connect the expansion water injection cavity and the low-pressure balloon expansion water hole, the potion or feces flushing water liquid delivery tube being configured to connect the potion or feces flushing water injection cavity and the potion or feces flushing water hole; and a low-pressure balloon, being disposed at the water outlet of the main tube and having a chamber connected to the expansion water injection cavity, expansion and contraction of the low-pressure balloon being adapted to be controlled by injecting expansion water into or extracting expansion water from the chamber;

wherein the expansion water injection cavity of the integrated connector injects expansion water by using an injection syringe for preventing excessive expansion, and the injection syringe for preventing excessive expansion has a water discharge hole at a scale marking above 46 ml.

17. The stool drain assembly of claim 16, further comprising a collection bag connector configured to be opened or closed, wherein the collection bag connector configured to be opened or closed has a connection port, a stool discharging port, and a plunger disposed between the connection port and the stool discharging port, the connection port is configured to be connected with the integrated connector, the stool discharging port is configured to be provided with a stool collection bag, and the plunger is configured to control a connection between the connection port and the stool discharging port.

18. The stool drain assembly of claim 16, wherein the convex ring-shaped waterflow loop is arranged circularly within the chamber of the low-pressure balloon.

19. The stool drain assembly of claim 16, wherein the at least two liquid pipes are embedded within the tube wall.

20. The stool drain assembly of claim 16, further comprising a temperature sensor, wherein the temperature sensor is embedded within the water outlet of the main tube.

* * * * *